United States Patent [19]

Liebenow et al.

[11] 4,420,488
[45] Dec. 13, 1983

[54] QUATERNARY 1,1-DIPHENYL-4-PYRROLIDINIUM-2-BUTYNE SALTS, A PROCESS FOR THEIR PRODUCTION AND MEDICAMENTS CONTAINING THESE COMPOUNDS

[75] Inventors: Walter Liebenow; Hans Liedtke, both of Nuremberg, Fed. Rep. of Germany

[73] Assignee: Ludwig Heumann & Co. GmbH, Nuremberg, Fed. Rep. of Germany

[21] Appl. No.: 243,618

[22] Filed: Mar. 13, 1981

[30] Foreign Application Priority Data

Mar. 17, 1980 [DE] Fed. Rep. of Germany ....... 3010152

[51] Int. Cl.³ .................... A61K 31/40; C07D 207/04
[52] U.S. Cl. .................................... 424/274; 548/574
[58] Field of Search ................ 260/326.5 R; 424/274; 548/574

[56] References Cited

U.S. PATENT DOCUMENTS 2,584,429 2/1952 Croxall et al. ............... 260/326.5 R
3,051,714 8/1962 Biel ............................. 260/326.5 R
4,001,328 1/1977 Molloy ....................... 260/326.5 R

FOREIGN PATENT DOCUMENTS 601311 7/1960 Canada .............................. 548/574
2142M 11/1963 France .

OTHER PUBLICATIONS

M. Negwer, Organisch-Chemische Arzneimittel und dhre Synonyma, Band II, p. 771 (1978), Akad.-Verlag, Berlin.
J. A. Gautier and C. C. Farnoux, Bul. Soc. Chim. France, p. 2147 (1964).
Konzett; H. and Rossler; R., Arch. Exp. Pharmacol. Path., 195, 71 (1940).
Takagi; K. and Okabe; S., Jap. J. Pharmac., 18, 9 (1968).
Brown; D. M. and Quinton; R. M., Brit. J. Pharmacol. 12, 53 (1957).
Pulewka; P., Arch. Exp. Pharmacol. Path. 168, 307 (1932).
Van Rossum; J. M., Arch. Int. Pharmacodyn. Ther. 143,299 (1963).
Engler; H. and Fritschi; E., Naunyn, Schmiedeberg's Arch. Pharmacol. 297, R 43 (1977).
"Organikum, Org.-Chemisches Grundpraktikum", Autorenkollektiv, VEB Deutscher Verlag der Wissenschaften, Berlin 1977, p. 260.

*Primary Examiner*—Donald G. Daus
*Assistant Examiner*—M. C. Eakin
*Attorney, Agent, or Firm*—Burns, Doane, Swecker & Mathis

[57] ABSTRACT

Quaternary 1,1-diphenyl-4-pyrrolidinium-2-butyne salts corresponding to the following general formula

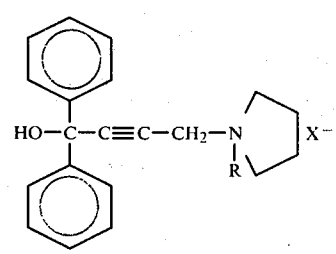

(I)

in which R represents methyl or ethyl and X is a chlorine or bromine atom, are described. These compounds are distinguished by improved spasmolytic and broncholytic activity.

3 Claims, No Drawings

QUATERNARY 1,1-DIPHENYL-4-PYRROLIDINIUM-2-BUTYNE SALTS, A PROCESS FOR THEIR PRODUCTION AND MEDICAMENTS CONTAINING THESE COMPOUNDS

This invention relates to quaternary 1,1-diphenyl-4-pyrrolidinium-2-butyne salts corresponding to the following general formula

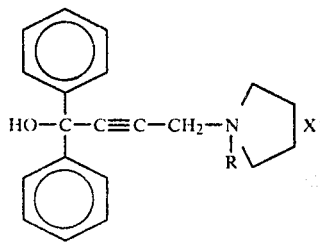

to a process for their production and to medicaments containing these compounds.

It is known that the phosphate of 1,1-diphenyl-4-pyrrolidino-2-butyne-1-ol (butynoline) having the following structural formula

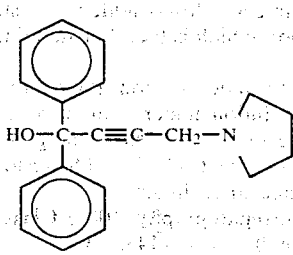

is pharmacologically active and shows for example anti-cholinergic spasmolytic and anti-ulcerogenic activity. By virtue of these properties, medicaments containing butynoline phosphate as their active principle are already available on the market.

It has now surprisingly been found that quaternary butynoline salts corresponding to the above formula show better pharmacological activity than the known butynoline phosphate.

Accordingly, the present invention relates to quaternary 1,1-diphenyl-4-pyrrolidinium-2-butyne salts corresponding to the following general formula

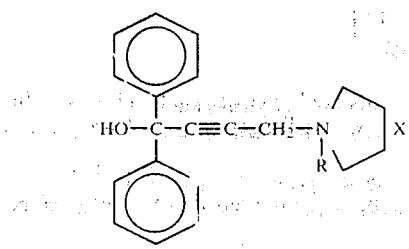

in which R represents methyl or ethyl and X is a chlorine or bromine atom.

These salts are new compounds. Compared with the known butynoline phosphate, they show for example improved spasmolytic and broncholytic activity.

The compound 1,1-diphenyl-4-pyrrolidinyl-2-butyne-1-ol-N-methyl ammonium bromide is preferred by virtue of its pharmacological properties.

The present invention also relates to a process for preparing these quaternary salts which is characterised in that 1,1-diphenyl-4-pyrrolidino-2-butyne-1-ol corresponding to the following formula is

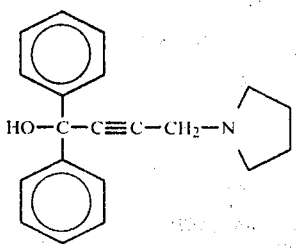

is reacted in known manner with an alkylating agent corresponding to the following formula

R—X in which R represents methyl or ethyl and X is a chlorine or bromine atom, in an aprotic or protic solvent to form the corresponding salts of formula I.

The reaction starts out from the known compound butynoline of which the production is described by J. A. Gautier and C. C. Farnoux in Bul. Soc. Chim. France 1964, page 2147.

Quaternization of the butynoline base is carried out by standard methods of the type described for example in "Organikum, Org.-chemisches Grundpraktikum", Autorenkollektiv, VEB Deutscher Verlag der Wissenschaften, Berlin 1977, page 260. Suitable solvents for the quaternisation reaction are both protic and aprotic solvents, such as for example ethanol, nitromethane, acetonitrile and dimethyl formamide. The reaction is best carried out with a molar ratio of butynoline base to alkyl halide of from 1.1 to 1:6, preferably 1:2. The reaction is preferably carried out in an autoclave under an excess pressure of from 0.5 to 5 bars, preferably 2 bars. The reaction is carried out at temperatures in the range from 65° to 75° C. and preferably at 70°. The reaction is usually over after 5 to 8 hours and normally after 7 hours. The reaction mixture is worked up by known methods, for example by distilling off the solvent, optionally in vacuo, adding an organic solvent and precipitating the product with an organic solvent miscible with that solvent. Purification is also carried out in known manner, for example by recrystallization from an organic solvent, such as ethanol, or by dissolution and reprecipitation.

As already mentioned, the compounds according to the invention show better pharmacological properties than the known butynoline phosphate, particularly in regard to the broncholytic and anti-ulcerogenic effect obtainable therewith. Tests relating to inhibition of the carbachol-induced secretion of saliva and mydriasis have shown that the compounds according to the invention have fewer side effects than the known butynoline phosphate.

The following Table summarizes the results of pharmacological studies conducted with the compound according to the invention, 1,1-diphenyl-4-pyrrolidinyl-2-butyne-1-ol-N-methyl ammonium bromide, and with butynoline phosphate as the comparison substance.

TABLE

| | 1,1-diphenyl-4-pyrrolidinyl-2-butyne-1-ol-N—methyl ammonium bromide | Butynoline phosphate | Test method (literature ref.) |
|---|---|---|---|
| Broncholysis (guinea pig) | $ED_{50}$ (μg/kg i.v.) ACH 30 Hi 500 | $ED_{50}$ (μg/kg i.v.) ACH 60 Hi 1000 | Konzett, H., Rossler, R., Arch. exp. Pharmacol. Path., 195, 71 (1940) |
| Anti-ulcerogenic effect stress ulcer | $ED_{50}$ (mg/kg) i.g. 25 | $ED_{50}$ (mg/kg) i.g. 150 | Takagi, K., Okabe, S., Jap. J. Pharmac. 18, 9 (1968) |
| Inhibition of the carbachol-induced secretion of saliva (rat) cholinolytic side effects | $ED_{50}$ (mg/kg) i.g. 24 | $ED_{50}$ (mg/kg) i.g. 9.8 | Mod. according to Brown, D. M., Quinton, R. M., Brit. J. Pharmacol. 12, 53 (1957) |
| Mydriasis cholinolytic side effects | $ED_{50}$ (mg/kg) i.g. 128 | $ED_{50}$ (mg/kg) i.g. 16 | Pulewka, P. Arch. exp. Pharmacol. Path. 168, 307 (1932) |
| Spasmolytic effect in vitro (Mee-ileum) | $pA_2$ (ACH) 8.0 | $pA_2$ (ACH) 8.2 | Van Rossum, J. M., Arch. Int. Pharmacodyn. Ther. 143, 299 (1963) |
| Inhibition of the carbachol-induced gastric secretion (Heidenhain cat) | $ED_{50}$ (mg/kg) i.g. 0.3 | $ED_{50}$ (ACH) i.g. 0.3 | Engler, H., Fritschi, E., Naunyn Schmiedeberg's Arch. Pharmacol. 297, R 43 (1977) |

Accordingly, the present invention also relates to a medicament, particularly a spasmolytic and anti-ulcerogenic agent, which is characterized in that it contains a quaternary salt of the type defined above in addition to standard auxiliaries and excipients.

The medicaments according to the invention may be made into pharmaceutical preparations with direct or delayed release of the active principle in admixture with an organic excipient or inorganic inert excipient suitable for oral or parenteral application, for example calcium hydrogen phosphate, cellulose, dextrose, corn starch, saccharose, magnesium stearate, lactose, gelatin, polyvinyl pyrrolidine, vegetable oils, polyethylene glycol, vaseline, etc. The medicament according to the invention may be made up in solid form, for example in the form of tablets or capsules, in the form of a solution, suspension or emulsion or in the form of suppositories. In addition, the medicament according to the invention may form the active principle of a tea preparation known per se. With peroral administration, the individual dose, based on the active principle, amounts to between 5 and 50 mg and preferably to between 10 and 30 mg. The daily dose may be administered in one or more individual doses.

The invention is illustrated by the following Example.

EXAMPLE

Preparation of 1,1-diphenyl-4-pyrrolidinyl-2-butyne-1-ol-N-methyl ammonium bromide 29.1 g (0.1 mole) of 1,1-diphenyl-4-pyrrolidino-2-butyne-1-ol are initially introduced into a 0.5-liter laboratory autoclave, suspended while stirring in 140 ml of dimethyl formamide and the resulting suspension cooled with acetone/dry ice to approximately −40° C. 19.0 g (0.2 mole) of methyl bromide are then added and the autoclave is closed.

After heating for 7 hours with stirring to 70° C., the reaction mixture is left to cool and the dimethyl formamide is evaporated off in a water jet pump vacuum in a rotary evaporator. 30 ml of 99.7% ethanol are then added and dissolved in a water bath heated to 60° C. 50 ml of ethyl acetate are slowly added with stirring to the resulting solution which is then left standing to crystallize.

After filtration under suction, the product is recrystallized by dissolution under heat in 50 ml of 99.7% ethanol, cooling to +10° C. and adding 60 ml of ethyl acetate and 30 ml of diethyl ether. The residue is filtered under suction and dried in air.

Thin-layer chromatography (100% $CH_3OH$) 1 patch.
Melting point: 147.8° C.–148.7° C.
Yield: 30.6 g=79.2% of the theoretical.

We claim:

1. A method of treating a warm-blooded mammal, comprising administering to a warm-blooded mammal an anti-ulcerogenically effective amount of a quaternary 1,1-diphenyl-4-pyrrolidinium-2-butyne salt of the formula:

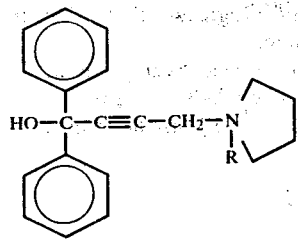

(I)

in which R represents methyl or ethyl and X is a chlorine or bromine atom, to elicit an anti-ulcerogenic response.

2. The method of claim 1 in which the salt is 1,1-diphenyl-4-pyrrolidinyl-2-butyne-1-ol-N-methyl ammonium bromide.

3. The method of claim 1 in which the salt is administered with a pharmaceutically acceptable carrier therefor.

* * * * *